United States Patent
Nelson et al.

(10) Patent No.: US 6,957,564 B2
(45) Date of Patent: Oct. 25, 2005

(54) IMPACT PROTECTION OF AN EXHAUST SENSOR

(75) Inventors: Charles Scott Nelson, Clio, MI (US); Mark R. McClanahan, Goodrich, MI (US); David K. Chen, Rochester Hills, MI (US); Russell H. Bosch, Gaines, MI (US)

(73) Assignee: Delphi Technologies, Inc., Troy, MI (US)

(*) Notice: Subject to any disclaimer, the term of this patent is extended or adjusted under 35 U.S.C. 154(b) by 234 days.

(21) Appl. No.: 10/373,491

(22) Filed: Feb. 25, 2003

(65) Prior Publication Data

US 2004/0163468 A1 Aug. 26, 2004

(51) Int. Cl.⁷ .............................. G01H 27/00
(52) U.S. Cl. .................... 73/23.31; 374/144
(58) Field of Search ............ 73/23.31, 23.32, 73/23.33, 866.5, 431; 374/144, 208, 209

(56) References Cited

U.S. PATENT DOCUMENTS

| | | | |
|---|---|---|---|
| 5,823,680 A | * | 10/1998 | Kato et al. .................. 374/185 |
| 5,880,353 A | * | 3/1999 | Graser et al. ................ 73/23.2 |
| 6,358,383 B2 | | 3/2002 | Nelson et al. |
| 6,360,581 B1 | * | 3/2002 | Murase et al. ............... 73/23.2 |
| 6,484,561 B2 | | 11/2002 | Jackson et al. |
| 6,527,928 B1 | * | 3/2003 | Watanabe et al. ........... 204/424 |
| 6,544,467 B2 | | 4/2003 | Symons et al. |
| 6,551,498 B2 | | 4/2003 | Nelson |
| 6,562,215 B1 | | 5/2003 | Nelson et al. |
| 6,585,872 B2 | | 7/2003 | Donelon et al. |

* cited by examiner

*Primary Examiner*—Robert Raevis
(74) *Attorney, Agent, or Firm*—Jimmy L. Funke

(57) ABSTRACT

Disclosed herein is an impact absorber for an exhaust sensor. The impact absorber comprises a collar of deformable material disposed around a housing of the exhaust sensor. The collar extends radially outward from the housing. The collar may be formed from a material selected to degrade at exhaust temperature, or the collar may be formed from a material that provides radiation shielding to a portion of the sensor after installation. The collar may be disposed around a sealing gasket. A wall may be disposed around at least a portion of a perimeter of the collar, the wall being spaced apart from a plurality of facets formed on the housing to form a recess for receiving a socket wrench tool.

14 Claims, 3 Drawing Sheets

IMPACT PROTECTION OF AN EXHAUST SENSOR

BACKGROUND OF THE INVENTION

Sensors are used in the automotive industry to sense amounts of oxygen, hydrocarbons, nitrous oxide (NOx), and other materials present in exhaust gases. Sensors are also used to measure other properties of exhaust gasses, such as temperature. These sensors may include various electrodes, contacts, conductors, structural elements, and other materials and systems. Sensors may also include electrochemical cells, thermocouples, heaters, conduits, various electrodes, particulate detectors, conductivity cells, one or more catalysts or catalytic elements, and the like, either alone or in various combinations. The operational conditions under which such sensors operate may require the sensor to be encased within a package that is capable of allowing the sensor to function despite the vibrations, temperature extremes, and other environmental concerns surrounding components that operate as part of an automotive and/or other exhaust gas system.

To function properly, the sensor must be properly installed and or attached to an exhaust system. Such installation may take place on an assembly line, in an automotive repair facility, or other similar environments. Installation of a sensor may include tightening, welding and/or the like of the sensor into an appropriate location in an exhaust system. Such environments and conditions may not be conducive to gentle handling of such a complicated and potentially fragile device, and the sensors may be dropped, abraded, and/or impacted during installation. To insure that the sensor survives such impacts, the sensor may be drop tested to insure that it survives impacts and other treatments that may be experienced during assembly. One method of impact testing sensors includes drop testing, wherein the sensor is dropped from a distance of about 1 meter onto a hard surface. The sensor is then evaluated for operability after successive drops are made. It is desirable for a sensor to be suitable for use after being dropped five (5) times. This drop test may be repeated using several sensors of a particular design due to the variability of how and where the sensor is exposed to the full impact of the fall during any one test. After the sensor is installed, it is subjected to different destructive forces. For example, the sensor may be subjected to heat radiated by the exhaust system. Radiated heat can cause degradation of the materials used in the sensor. Accordingly, protection of a sensor from otherwise destructive forces prior to, during, and after installation of the sensor would be beneficial.

SUMMARY OF THE INVENTION

Disclosed herein is an impact absorber for an exhaust sensor. The impact absorber comprises a collar of deformable material disposed around a housing of the exhaust sensor. The collar extends radially outward from the housing.

In one embodiment, the collar is formed from a material selected to degrade at exhaust temperature. In another embodiment, the collar is formed from a material selected to withstand exhaust temperature, the collar being positioned to protect a portion of the exhaust sensor from radiated heat. In another embodiment the collar is disposed around a sealing gasket, the sealing gasket being disposed around the housing. In another embodiment, an outer edge of the collar is bent. In yet another embodiment, a wall is disposed around at least a portion of a perimeter of the collar, the wall being spaced apart from a plurality of facets formed on the housing to form a recess for receiving a socket wrench tool.

The above-described and other features will be appreciated and understood by those skilled in the art from the following detailed description, drawings, and appended claims.

BRIEF DESCRIPTION OF THE DRAWINGS

Referring now to the figures wherein the like elements are numbered alike.

DESCRIPTION OF THE PREFERRED EMBODIMENT

Figure 1:
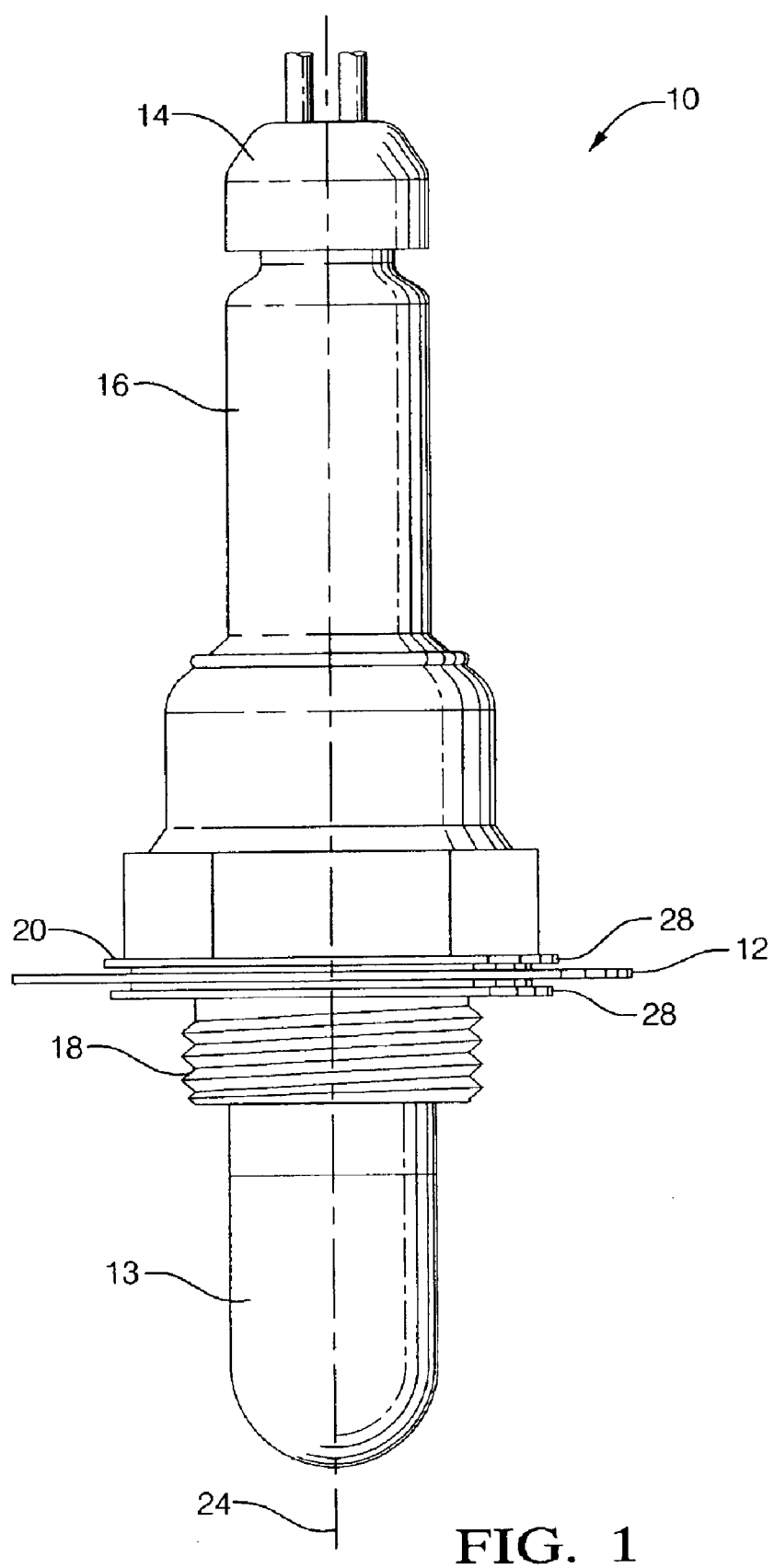
FIG. 1 is an elevation view of a sensor including a first embodiment of an impact absorber.

Exhaust sensors require protection from impact due to dropping and other potentially harmful contact that may be experienced prior to and during installation. Referring to FIG. 1, an example of an exhaust gas sensor 10 including an impact absorber 12 is shown generally at 10. Exhaust gas sensors 10 may include a sensing end 13 which is placed in contact with the exhaust gas to be sensed, and a connector end 14 provided with various electrical contacts, circuits, fluid conduits, and the like. The connector end 14 thus allows the sensor 10 to function by providing electricity, reference gases, and the like to the sensor, and also may provide for the measurements and other electric signals obtained using the sensor 10 to be communicated to another location.

Exhaust gas sensor 10 may be provided with fittings, threaded members, and the like to allow the sensor 10 to be installed and then subsequently removed and/or replaced from an end use situation. For example, sensor 10 may be equipped with a sensor housing 16 which includes a threaded, tapered, or the like portion 18, which is dimensioned so as to allow the sensor to be secured and/or attached to an exhaust gas system. In addition, a gasket 20 or other type of sealing device (e.g., a seat gasket) may be disposed between a mating surface of the sensor housing 16 and the corresponding exhaust gas system to ensure a leak-proof fit once the sensor 10 is installed.

Figure 2:
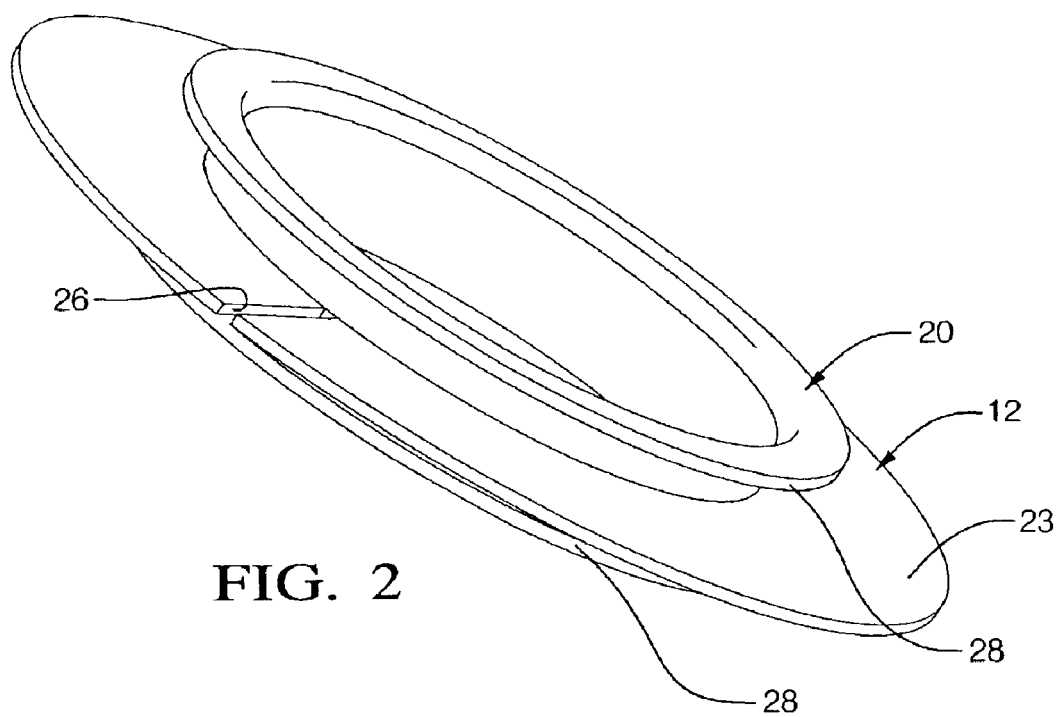
FIG. 2 is a perspective view of the first embodiment of the impact absorber.

It has been discovered that an impact absorber 12 disposed at least partially around an exhaust gas or other type of sensor 10 can provide protection of the sensor from impacts associated with packaging, shipping, and handling of the sensor 10, as well as protection from being dropped, or otherwise impacted during installation. In addition to providing impact protection, the impact absorber may also provide radiation shielding to the sensor 10 when the sensor 10 is installed in the exhaust system. Referring to FIGS. 1 and 2, the impact absorber 12 includes a collar 23 in the form of a concentric ring or other geometric shape, arranged on or around the sensor 10 to depend outwardly from an axis of the sensor 10. In addition to the collar 23 being at least partially circular, it may also be square, triangular, or any of the various geometric shapes, both regular (all sides having the same dimension, such as hexagonal and octagonal) and irregular (all sides not being of the same dimension, including star shaped, crescent shaped, and the like). In addition, various combinations of shapes may be used, either combined to form a single shape, or being separate impact absorbing barriers disposed in unison about the collar 23. The impact absorber 12 may comprise a single collar 23 disposed in a single location on the sensor 10, or may comprise a plurality of collars 23 disposed in one or more locations along at least one axis of the sensor 10.

The collar 23 comprises a layer or layers of at least one deformable material. The deformable material may have a resiliency sufficient to at least partially support the sensor 10, while being deformable enough to absorb the impact energy of the sensor 10 hitting a hard surface such that a force transferred to a sensor 10 resulting from an impact imparted to the sensor 10 is lessened, as compared to a sensor 10 treated the same way in the absence of such an impact absorber.

The impact absorber 12 may comprise metal, paper, polymeric foam, rubber, starch, metal foil, and/or combinations thereof, and the like. The material selected may be capable of withstanding the temperature and operational conditions of an exhaust gas system. Such material would be advantageous where the impact absorber 12 is to shield the sensor 10 from heat radiated from the exhaust system. Alternatively, the material may be consumed (e.g., oxidized or burned off) during normal operation of the exhaust system once the sensor 10 has been installed, as at that time the impact absorber 12 may no longer serve a purpose. The impact absorber 12 may include a perforation 26, or other deformity or relief disposed within the collar 23 to allow facile installation of the impact absorber 12 before installation of the sensor 10 and/or removal of the impact absorber 12 once the sensor 10 is at least partially installed.

The dimensions of the impact absorber 12 preferably allow for the sensor 10 to be adequately protected from impact, while allowing the sensor 10 to be at least partially installed without removal of the impact absorber 12. Accordingly, the impact absorber 12 is preferably dimensioned such that upon dropping of the sensor 10 onto a surface, the impact absorber 12 comes in contact with the surface in such a way that the impact of the drop is absorbed by the impact absorber 12 alone, or in tandem with the sensor 10. Accordingly, the impact absorber 12 is preferably located on the sensor 10 such that a portion of the sensor 10 more prone to damage by impact is protected from impact to a greater extent than an end of the sensor 10 less susceptible to damage resulting from an impact. In addition to being dimensioned and positioned to provide impact resistance, the dimensions and position of the impact absorber 12 may be selected such that the impact absorber 12 shields the sensor 10 from heat radiated by the exhaust system. Where the impact absorber 12 is to provide heat shielding, a width of the impact absorber 12 may be increased, and the impact absorber 12 is preferably positioned between the exhaust system and a portion of the sensor 10 susceptible to damage from radiated heat. For example, the position of the impact absorber 12 shown in FIG. 1 provides shielding to the upper portion of housing 16 and the connector end 14 of sensor 10, which are susceptible to degradation from radiated heat.

The impact absorber 12 may include an essentially flat collar 23, or the collar 23 may be convoluted, serpentine, bent, and/or folded. The collar 23 may also include a plurality of ribs, supports, and/or folds, and/or the collar 23 may also define a continuous solid sheet, or a discontinuous sheet comprising a plurality of voids disposed within the layer of deformable material.

The width of the collar 23, measured perpendicular to the central axis 24 (e.g., diametrically in the circular-shaped embodiment shown), is selected such that it provides adequate protection to the sensor 10. For example, the width of the collar 23 may be selected such that the collar 23 extends radially outward from central axis 24 further than any portion of the housing 16. Preferably, the width of the collar 23 is greater than or equal to about 1.1 times the width of the widest portion of the housing 16. More preferably, the width of the collar 23 is greater than or equal to about 1.4 times the width of the widest portion of the housing 16. The width of the collar 23 is dependent on various factors, including, for example, the material used in the collar 23, the geometry of the collar 23, and whether the collar 23 is to provide heat shielding after installation.

The thickness of the collar 23, as measured perpendicular to its width, preferably allows for the sensor 10 to be adequately protected from impact, while allowing the sensor 10 to be installed without removal of the impact absorber 12. The collar 23 thickness may be about 0.1 to about 10 millimeters (mm) thick. Within this range, a thickness of less than or equal to about 5 mm is preferred with less than or equal to about 2 mm especially preferred. Also within this range, a thickness of greater than or equal to about 0.1 mm is preferred with greater than or equal to about 1 mm especially preferred. The thickness of the collar 23 is dependent on various factors, including, for example, the material used in the collar 23 and the geometry of the collar 23.

The impact absorber 12 may be disposed directly about the periphery of the sensor 10, and/or may be physically attached to a portion of the sensor 10. It may also be disposable onto the sensor 10 such that directly prior to the sensor 10 being installed, the sensor 10 is fitted with an impact absorber 12. In the embodiment shown in FIG. 2, the impact absorber 12 is attached to the seat gasket 20, extending essentially radially out from a central axis 24 of the sensor 10. In this embodiment, the impact absorber 12 is thin, such that it does not add of thickness to the gasket 20. When the gasket 20 is pressed into place (by installing the sensor 10), the impact absorber 12 is trapped between two folds 28 of the seat gasket 20.

Figure 3:
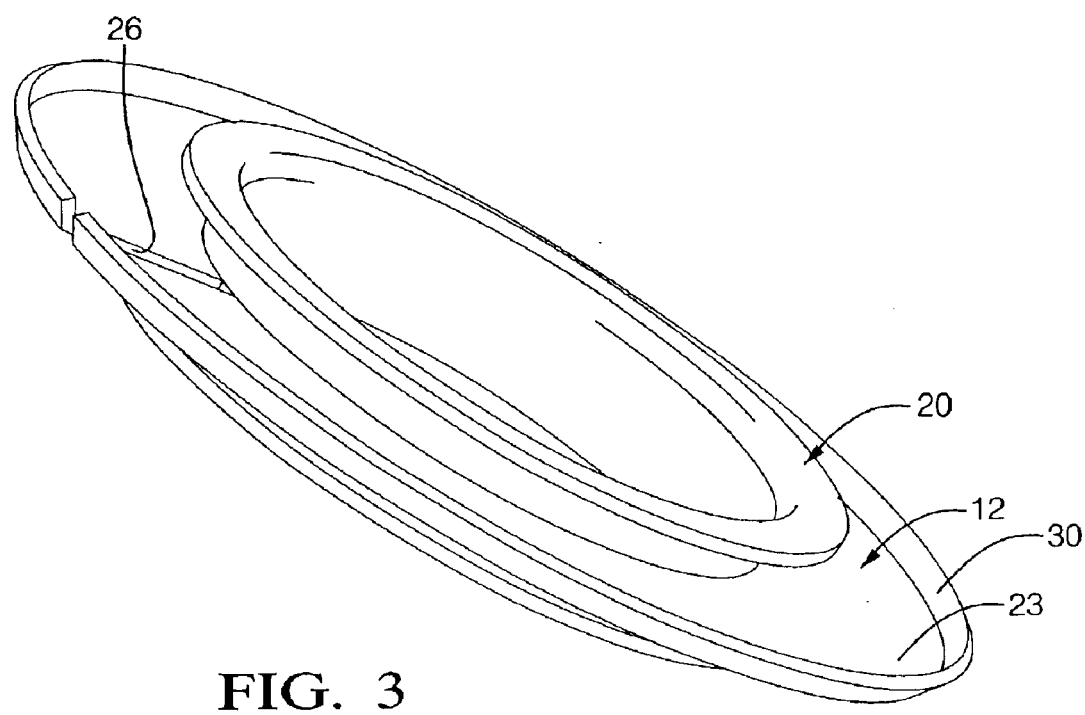
FIG. 3 is a perspective view of a second embodiment of the impact absorber.

Referring to FIG. 3, an embodiment is shown where impact absorber 12 includes a curved edge 30 disposed around the perimeter of collar 23. If the sensor 10 is dropped, the hard surface will impact the curved edge 30, and at least a portion of the impact from the fall will be absorbed by a bending of the material forming the impact absorber 12.

Figure 4:
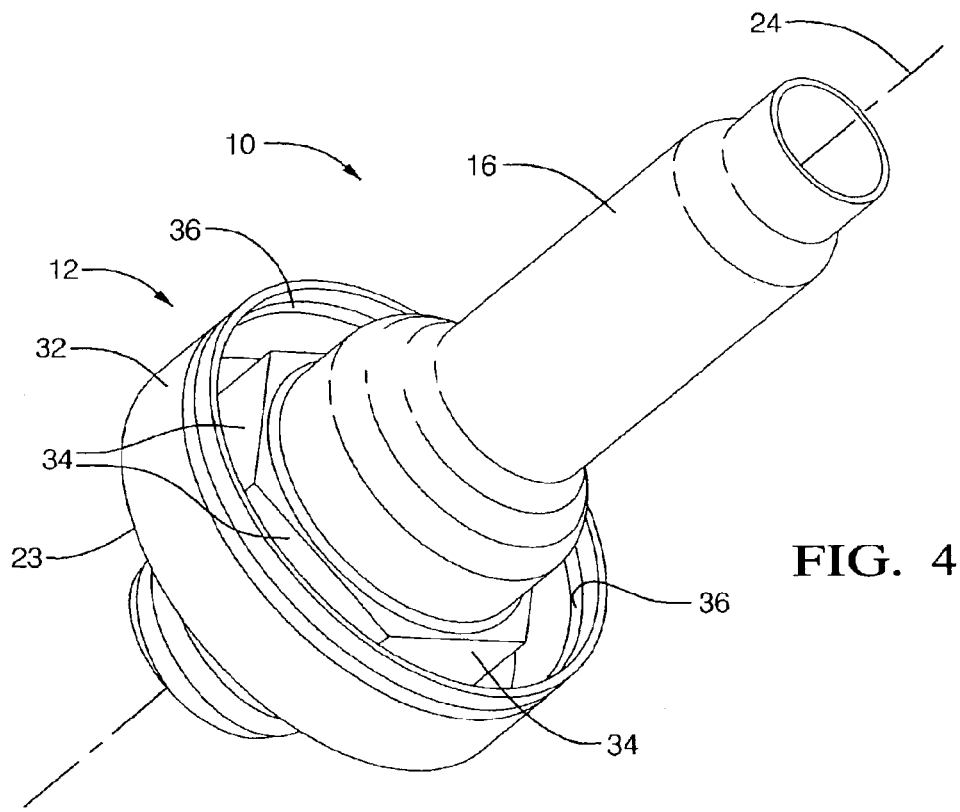
FIG. 4 is a perspective view of a third embodiment of the impact absorber.

Referring to FIG. 4, an embodiment is shown where curved edge 30 is extended to form a wall 32, which extends in a direction generally parallel to central axis 24. Wall 32 is spaced apart from a plurality of facets 34 formed on the housing 16 to form a recess for receiving a socket wrench tool. The distance between the wall 32 and the facets 34 may be selected to provide an interference fit between the wall 32 and the socket wrench tool to releasably retain the sensor 10 in the socket wrench tool during installation of the sensor 10. In addition, a bump 36 may be formed on the wall 32 to increase the resistance between the socket wrench tool and the wall 32 for grabbing onto the socket wrench tool during installation of the sensor 10.

Figure 5:
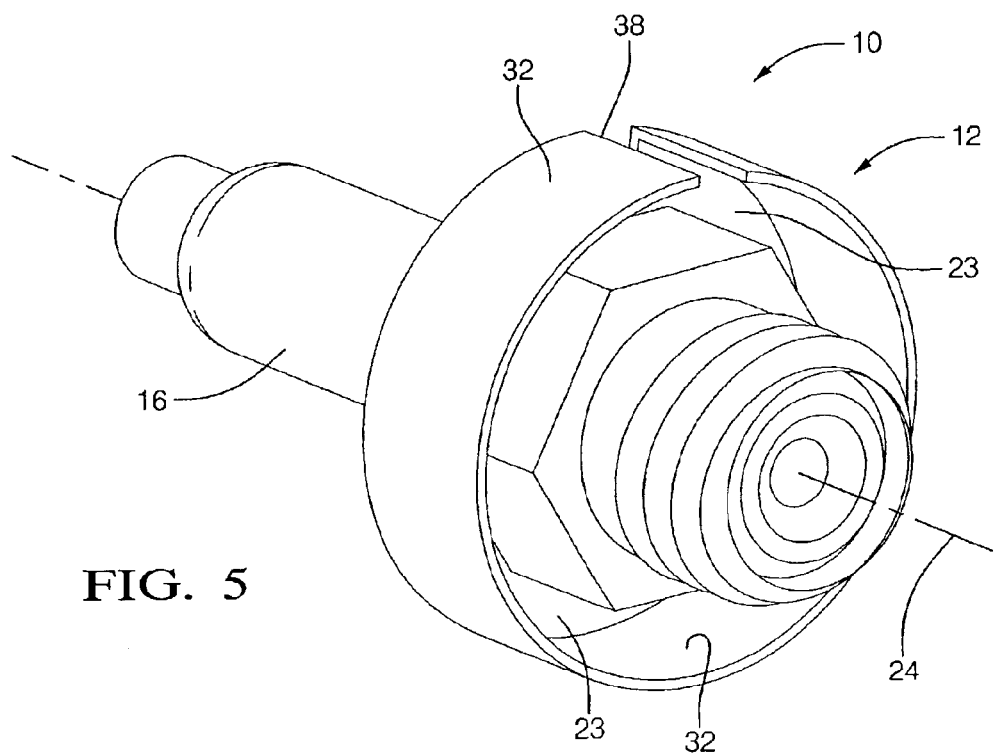
FIG. 5 is a perspective view of a fourth embodiment of the impact absorber.

Referring to FIG. 5, another alternative embodiment of impact absorber 12 is shown in which impact absorber 12 is disposed around an upper shield portion of housing 16. Impact absorber 12 may be formed from plastic, and a slot 38 maybe disposed in impact absorber 12 to allow impact absorber 12 to be snapped into place on the housing 16.

Use of the above described impact absorber may provide protection from impact due to drops during installation. Impact protection of the magnitude required to protect a sensor during a drop may only be required during installation. Accordingly, the use of the impact absorber 12 disclosed herein may allow for designs directed more to the vibration and other energy events that occur during normal use, which possess lower impulse energy than the energy associated with a sensor being dropped. In addition, by using materials that are oxidized at exhaust system temperatures, the impact absorbers described herein may be removed during normal use, wherein it no longer serves a useful purpose. The above described impact absorber may also remain in place after installation to act as a radiation shield for protecting the sensor from heat radiated by the exhaust system.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An impact absorber for an exhaust sensor, the impact absorber comprising:

a collar of deformable material disposed around a housing of the exhaust sensor, the collar extending radially outward from the housing, wherein the collar bends to absorb at least a portion of an impact force resulting from the exhaust sensor being dropped;

wherein the collar is formed from a material selected to degrade at exhaust temperature.

2. The impact absorber of claim 1, wherein the collar is at least partially bent.

3. The impact absorber of claim 1, wherein the collar further comprises a perforation, to allow for removal of the impact absorber.

4. The impact absorber of claim 1, wherein an outer edge of the collar is bent.

5. An impact absorber for an exhaust sensor, the impact absorber comprising:

a collar of deformable material disposed around a housing of the exhaust sensor, the collar extending radially outward from the housing, wherein the collar bends to absorb at least a portion of an impact force resulting from the exhaust sensor being dropped; wherein the collar is disposed around a sealing gasket, the sealing gasket being disposed around the housing.

6. An impact absorber for an exhaust sensor, the impact absorber comprising:

a collar of deformable material disposed around a housing of the exhaust sensor, the collar extending radially outward from the housing, wherein the collar bends to absorb at least a portion of an impact force resulting from the exhaust sensor being dropped; wherein a wall is disposed around at least a portion of a perimeter of the collar, the wall being spaced apart from a plurality of facets formed on the housing to form a recess for receiving a socket wrench tool.

7. The impact absorber of claim 6, wherein a bump is formed on the wall, the bump extending toward the plurality of facets to increase resistance between the socket wrench tool and the wall.

8. An exhaust sensor comprising:

a housing; and, a collar of deformable material disposed around the housing, the collar extending radially outward from the housing, wherein the collar bends to absorb at least a portion of an impact force resulting from the exhaust sensor being dropped; wherein the collar is formed from a material selected to degrade at exhaust temperature.

9. The exhaust sensor of claim 8, wherein the collar is at least partially bent.

10. The exhaust sensor of claim 8, wherein the collar further comprises a perforation to allow for removal of the impact absorber.

11. The exhaust sensor of claim 8, wherein the collar is disposed around a sealing gasket, the sealing gasket being disposed around the housing.

12. The exhaust sensor of claim 8, wherein an outer edge of the collar is bent.

13. The exhaust sensor of claim 8, wherein a wall is disposed around at least a portion of a perimeter of the collar, the wall being spaced apart from a plurality of facets formed on the housing to form a recess for receiving a socket wrench tool.

14. The exhaust sensor of claim 13, wherein a bump is formed on the wall, the bump extending toward the plurality of facets to increase resistance between the socket wrench tool and the wall.

* * * * *